United States Patent
Gong et al.

(10) Patent No.: US 10,292,848 B2
(45) Date of Patent: May 21, 2019

(54) HIGHLY RETRACTABLE INTRAVASCULAR STENT CONVEYING SYSTEM

(71) Applicant: SUZHOU INNOMED MEDICAL DEVICE CO., LTD., Suzhou, Jiangsu (CN)

(72) Inventors: Xiaoyan Shawn Gong, Jiangsu (CN); Xiang Zhou, Jiangsu (CN); Guanhua Xue, Jiangsu (CN); Weikun Zhou, Jiangsu (CN); Pengchong Qiu, Jiangsu (CN)

(73) Assignee: SUZHOU INNOMED MEDICAL DEVICE CO., LTD., Suzhou, Jiangsu (CN)

( * ) Notice: Subject to any disclaimer, the term of this patent is extended or adjusted under 35 U.S.C. 154(b) by 138 days.

(21) Appl. No.: 15/312,837

(22) PCT Filed: May 19, 2015

(86) PCT No.: PCT/CN2015/079270
§ 371 (c)(1),
(2) Date: Jan. 17, 2017

(87) PCT Pub. No.: WO2015/176643
PCT Pub. Date: Nov. 26, 2015

(65) Prior Publication Data
US 2017/0172773 A1    Jun. 22, 2017

(30) Foreign Application Priority Data
May 21, 2014    (CN) .......................... 2014 1 0215596

(51) Int. Cl.
*A61F 2/95*    (2013.01)
*A61F 2/962*   (2013.01)
(Continued)

(52) U.S. Cl.
CPC ................ *A61F 2/95* (2013.01); *A61F 2/962* (2013.01); *A61F 2/966* (2013.01); *A61M 25/00* (2013.01);
(Continued)

(58) Field of Classification Search
CPC .. A61F 2/95; A61F 2/962; A61F 2/966; A61F 2002/9665; A61F 2002/9517
See application file for complete search history.

(56) References Cited

U.S. PATENT DOCUMENTS

| 6,113,608 A | 9/2000 | Monroe et al. |
| 2005/0033402 A1 | 2/2005 | Cully et al. |

(Continued)

FOREIGN PATENT DOCUMENTS

| CN | 102283728 A | 12/2011 |
| CN | 102573702 A | 7/2012 |

(Continued)

OTHER PUBLICATIONS

International Search Report for PCT/CN2015/079270.
Extended European Search Report dated Jan. 4, 2018 for European Patent Application No. 15795551.9.

*Primary Examiner* — Katrina M Stransky
(74) *Attorney, Agent, or Firm* — K&L Gates LLP; Louis C. Cullman; Brian J. Novak

(57) ABSTRACT

A highly retractable intravascular stent delivery system, including a tube assembly and a rotation driving assembly. The tube assembly includes an outer tube 5, an intermediate tube 6, and inner tube 7, wherein an intravascular stent 3 and a stent retaining block 4 are provided within the outer tube 5. The rotation driving assembly includes a housing 9, an outer screw 19, and an intermediate screw 14 located within the housing 9, as well as a driving member. The driving member allows two screws to rotate at opposite directions, so as to drive the outer tube 5 to move toward the proximal (Continued)

end, and the intermediate tube 6 pushes the stent retaining block 4 and the intravascular stent 3 to move toward the distal end. The system uses three-lay tube structure and uses driving gear to drive two screws to move at directions opposite to each other, such that the intermediate tube 6 and the outer tube 5 are driven to move to directions opposite to each other. Therefore, the axial retraction of the intravascular stents can be effectively offset and axial movement of the intravascular stents due to axial retraction of the intravascular stents is avoided, thereby accurately implanting the stents into the body.

18 Claims, 11 Drawing Sheets

(51) Int. Cl.
  *A61F 2/966* (2013.01)
  *A61M 25/00* (2006.01)
  *A61M 25/01* (2006.01)

(52) U.S. Cl.
  CPC . *A61M 25/0102* (2013.01); *A61F 2002/9517* (2013.01); *A61F 2002/9665* (2013.01)

(56) References Cited

U.S. PATENT DOCUMENTS

| | | | |
|---|---|---|---|
| 2006/0204556 A1 | 9/2006 | Daniels et al. | |
| 2006/0282150 A1* | 12/2006 | Olson | A61F 2/966 623/1.11 |
| 2013/0274860 A1* | 10/2013 | Argentine | A61F 2/95 623/1.12 |
| 2014/0046429 A1* | 2/2014 | Cragg | A61F 2/966 623/1.12 |

FOREIGN PATENT DOCUMENTS

| | | |
|---|---|---|
| CN | 103025277 A | 4/2013 |
| CN | 103037814 A | 4/2013 |
| CN | 103096838 A | 5/2013 |
| CN | 103356316 A | 10/2013 |
| CN | 203388976 U | 1/2014 |
| CN | 103961194 A | 8/2014 |
| CN | 203885674 U | 10/2014 |
| EP | 1358903 A2 | 11/2003 |
| WO | 2002/087470 A1 | 11/2002 |
| WO | 2013/074662 A1 | 5/2013 |
| WO | 2013/154749 A1 | 10/2013 |
| WO | 2014/100596 A1 | 6/2014 |
| WO | 2015/038875 A1 | 3/2015 |
| WO | 2015/176643 A1 | 11/2015 |

\* cited by examiner

Prior Art

HIGHLY RETRACTABLE INTRAVASCULAR STENT CONVEYING SYSTEM

FIELD OF THE INVENTION

Generally, the present invention relates to the field of medical apparatus for minimal invasive surgery. In particular, the present invention relates to a delivery system for intravascular stents.

BACKGROUND OF THE INVENTION

Minimal invasive surgeries which utilize stents have a certain advantages such as small wound size, reduced complications, and satisfying prognosis, in comparison with traditional peripheral artery surgeries. Currently, minimal invasive surgeries become major methods for treating peripheral artery stenosis.

As shown in FIG. 1, a delivery system is needed to implant intravascular stents into a body. A delivery system being currently used is shown in Chinese Patent Application CN201110190183.4, which includes a hollow inner tube and an outer tube connected to each other. Guide wires used during surgery pass through the hollow portion in the inner tube and intravascular stents are disposed between the inner tube and the outer tube. When a surgery is being performed, a tube assembly of the delivery system can be introduced to the target treatment area by the guide wires, and then the outer tube is withdrawn by a control assembly, whereby the intravascular stents are unfolded and positioned on the intravascular walls. However most of the self-expandable stents cannot be accurately located by using such delivery systems due to high retractability and highly axial retractability of the stents. Therefore, such a delivery system doesn't meet the requirements for surgery. Chinese Patent No. 201310315654.9 owned by the present applicant reveals a delivery system for intravascular stents. However, it is difficult to manufacture a rotation driving assembly in such delivery system, and if such delivery system is used to position a stent with long axial length, it needs a hand shank with increased length. It is inconvenient for the doctors to operate such delivery system.

SUMMARY OF THE INVENTION

In one aspect, the present invention provides a delivery system with a novel structure, suitable for intravascular stents with high axial retractability.

The object of the present invention is achieved by the following solution:

A highly retractable intravascular stent delivery system is described, including a tube assembly and a rotation driving assembly, wherein the tube assembly extends into the rotation driving assembly and is driven by the rotation driving assembly.

The tube assembly includes an outer tube, an intermediate tube disposed within the outer tube, and an inner tube disposed within the intermediate tube, wherein the inner tube includes a hollow channel through which guide wires pass, and the delivery system is introduced to the target treatment area by the guide wires, and the outer tube includes an intravascular stent loading area within which the intravascular stent is placed; and a stent retaining block is abutted against the proximal end of the intravascular stent, the stent retaining block is fixed to the distal end of the intermediate tube; the distal end of the inner tube passes through the inner cavity of the stent retaining block and the intravascular stent and extends out of the distal surface of the outer tube.

The rotation driving assembly includes a housing, an outer screw and an intermediate screw disposed within the housing, and a driving member for driving the outer screw and the intermediate screw. Outer threads are provided on the outer surface of the outer screw that is threadably connected to an outer screw jaw. The outer screw jaw is non-movably connected to the outer tube through a connection tube for outer tube and outer threads are provided on the outer surface of the intermediate screw that is threadably connected to an intermediate screw jaw. The intermediate screw jaw is non-movably connected to the intermediate tube through a connection tube for intermediate tube. The outer screw and the intermediate screw are provided with left hand threads and right hand threads that are opposite to each other, respectively. The driving member drives the outer screw and the intermediate screw to rotate at opposite directions, and the rotation of the outer screw drives the outer screw jaw to move toward the proximal end. The rotation of the intermediate screw drives the intermediate screw jaw to move toward the distal end, such that the intermediate tube drives the stent retaining block and the intravascular stent to move toward the distal end.

In one embodiment, the driving member includes a manual knob for driving the rotation of a driving gear, which is positioned outside of the housing, and an entire rotation handle assembly rotatably disposed within the housing. The entire rotation handle assembly includes a driving gear located at the proximal end within the housing, a driven wheel for the outer screw, and a driven wheel for the intermediate screw, which are fitted with the driving gear. The driven wheel for the outer screw is non-movably connected to the proximal end of the outer screw. The driven wheel for the intermediate screw is non-movably connected to the proximal end of the intermediate screw.

In one embodiment, the driving member includes a second motor disposed at the end of the outer screw, a first motor disposed at the end of the intermediate screw and a switch disposed outside of the housing for controlling the second and the first motor.

In one embodiment, the thread pitch of the left hand threads provided on the outer screw is different from that of the right hand threads provided on the intermediate screw.

In one embodiment, a locking screw is configured at the distal end, outside of the housing.

In one embodiment, a guide groove for the outer screw jaw is configured within the housing. A connection apparatus for the outer screw jaw is configured on the outer screw jaw, such that the outer screw jaw moves along the guide groove for the outer screw jaw. A guide groove for the intermediate screw jaw is also configured within the housing. A connection apparatus for the intermediate screw jaw is configured on the intermediate screw jaw, such that the intermediate screw jaw moves along the guide groove for the intermediate screw jaw.

In one embodiment, a groove is formed on the outer wall of the connection tube for outer tube, adjacent to the intermediate screw jaw, for readily pushing the connection tube for intermediate tube.

In one embodiment, a guide sleeve is non-movably disposed at the proximal end of the inner tube, such that guide wires extend into the inner tube through the guide sleeve.

In one embodiment, a guide tube is disposed at the proximal end of the tube assembly, which is air-tightly connected to the tube assembly, and a cleaning valve is air-tightly and non-movably connected to the end of the guide tube.

In one embodiment, a hemostasis ring is disposed at the proximal end of the tube assembly.

The present invention has the following advantageous effects. The axial retraction of intravascular stents can be effectively offset by using a triple-layer tube structure and using the driving member to drive the intermediate tube and the outer tube to move in opposite directions, such that axial movement of the intravascular stents due to axial retraction of the intravascular stents is avoided, thereby accurately implanting the stents into the body. The delivery system has a balanced structure and is easy to manufacture. Further no interference due to axial movement occurs during operations.

BRIEF DESCRIPTION OF THE DRAWINGS

The present invention will be further described by reference to the following detailed description and the accompanying drawings of which.

The reference numbers are as follows: 1—tip, 2—radiopaque ring, 3—intravascular stent, 4—stent retaining block, 5—outer tube, 6—intermediate tube, 7—inner tube, 8—fixed sleeve, 9—housing, 10—locking screw, 11—manual knob, 12—cleaning valve, 13—connection tube for the outer tube, 14—intermediate screw, 15—connection apparatus for the intermediate screw jaw, 16—intermediate screw jaw, 17—driven wheel for the intermediate screw, 18—driving gear, 19—outer screw, 20—connection apparatus for the outer screw jaw, 21—outer screw jaw, 22—connection tube for the intermediate tube, 23—driven wheel for the outer screw, 24—guide groove for the outer screw jaw, 25—guide groove for the intermediate screw jaw, 26—guide sleeve, 27—groove, 28—first motor, 29—switch, 30—second motor, 31—hemostasis ring.

DETAILED DESCRIPTION OF THE INVENTION

Figure 1:
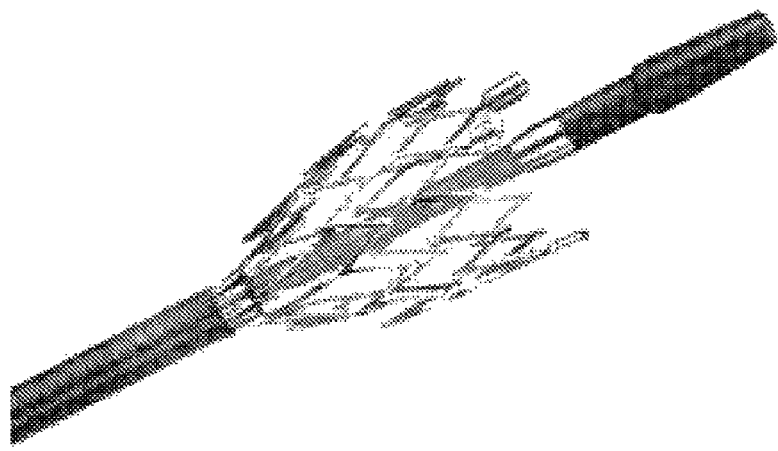
FIG. 1 is a use schematic drawing of the delivery system for a prior art intravascular stent.
Figure 2:
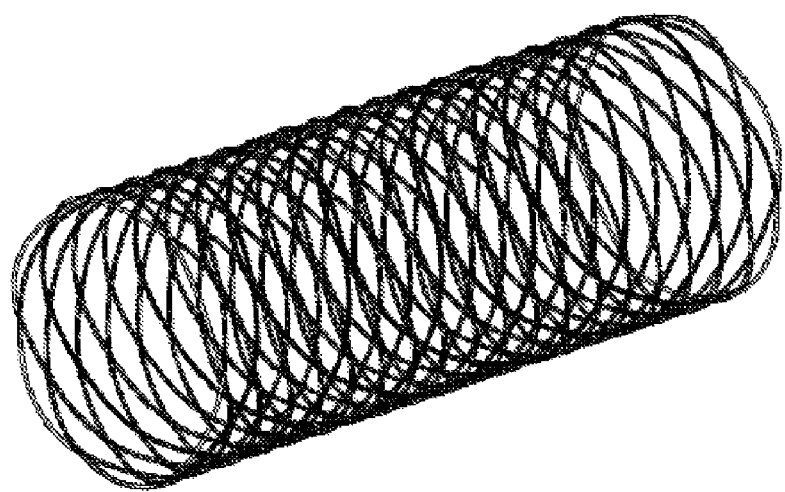
FIG. 2 is a schematic drawing of the intravascular stent with high axial retractability.
Figure 3:
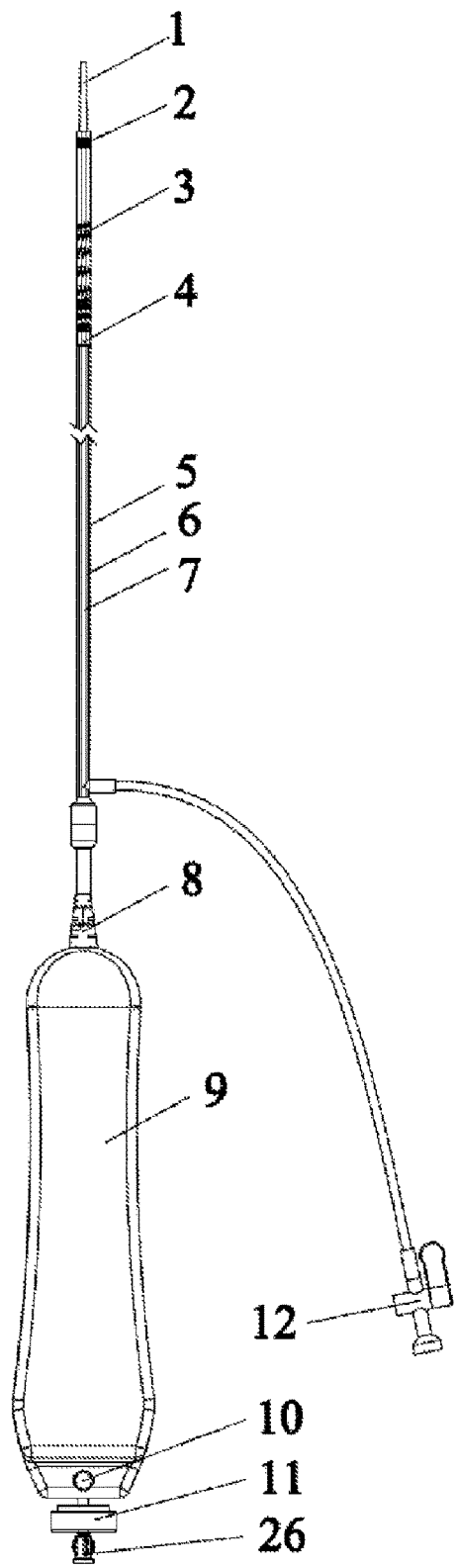
FIG. 3 is a schematic drawing of the delivery system according to an example embodiment.
Figure 4:
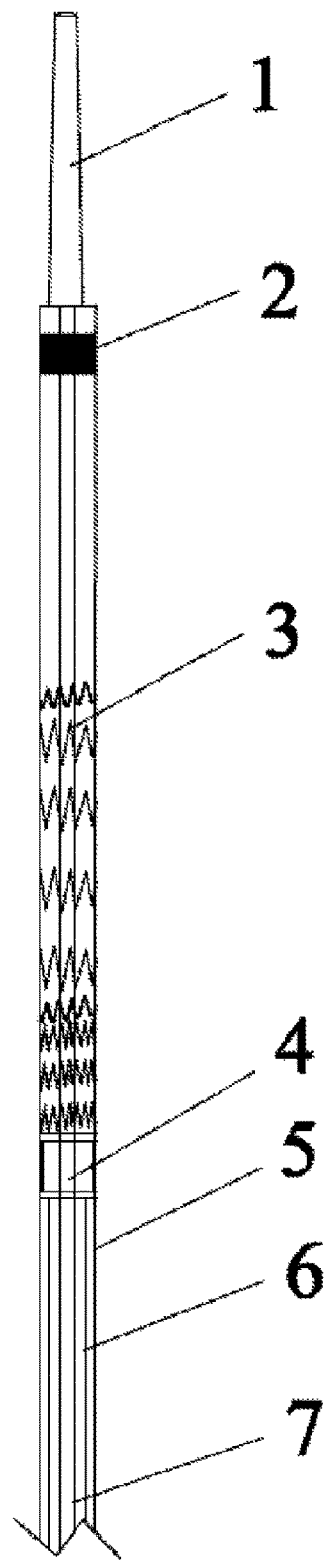
FIG. 4 is an enlarged structure drawing of the tube assembly.
Figure 5:
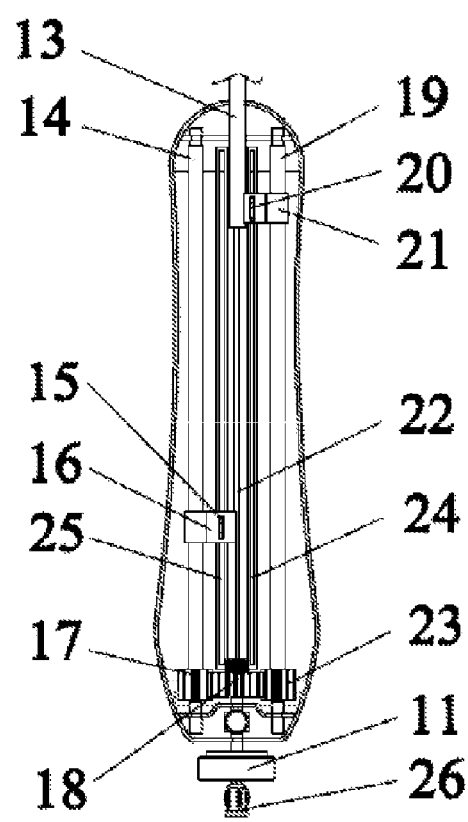
FIG. 5 is an inner structure schematic drawing of the rotation driving assembly.
Figure 6:
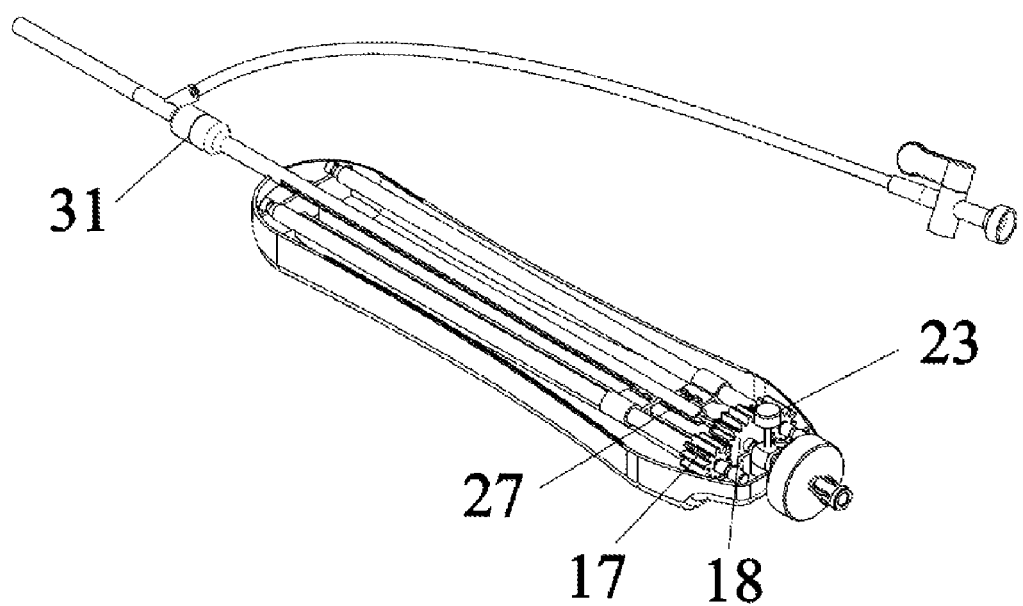
FIG. 6 is a three-dimensional structure drawing of the rotation driving assembly.

Described herein is a delivery system for intravascular stents with axial high retractability. As shown in FIG. 2, the intravascular stent with axial high retractability is formed by winding nickel-titanium alloy wires, including a cylindric main body and round corner portions disposed on the both ends of the main body. The main body is formed by forward and backward crossing and overlapping the nickel-titanium alloy wires. The main body is formed by a set of diamond grid units. There is no fixed limitation on the node overlapping on the diamond grid units of such intravascular stent. Such a node which lacks fixed limitation allows the nickel-titanium alloy wires to rotate and twist, rather than exhibit a circle movement. Therefore, such a configuration can avoid bending stress which is high, typically occurs around the node in a laser cutting stent. This mechanism can be shared by the same grid stent, but a new stent with closed-end circles and low corners, which is made from nickel-titanium alloy wires, can be the only stent with both radial rigidity and axial flexibility. As such, after implanting such an intravascular stent into a vessel, the stent is not formed as a conventional conical shape due to its excellent ductility, but formed as cylindric shape, which addresses the difficulties in the prior art.

FIGS. 3, 4, 5 and 6 show an example of a delivery system by which the intravascular stent as shown in FIG. 2 can be delivered into patient. The delivery system includes a tube assembly and a rotation driving assembly, and the tube assembly extends into the rotation driving assembly and is driven by the rotation driving assembly.

The tube assembly includes an outer tube 5, an intermediate tube 6 disposed within the outer tube 5, and an inner tube 7 disposed within the intermediate tube 6. The inner tube 7 includes a hollow channel allowing guide wires to pass therethrough. The guide wires introduce the delivery system into the target treatment area. The outer tube 5 includes an intravascular stent loading area. The intravascular stent 3 is placed in this loading area. A stent retaining block 4 is abutted against the proximal end of the intravascular stent 3. The stent retaining block 4 is fixed to the distal end of the intermediate tube 6. The distal end of the inner tube 7 passes through the stent retaining block and inner cavity of the intravascular stent 3 and extends out of the distal surface of the outer tube 5. Under circumstances where the intermediate tube 6 can support the intravascular stent 3, the stent retaining block 4 can be omitted.

A radiopaque ring 2 is sleeved on the outer tube 5 as an indication marker. A tip 1 for orientation is provided at the distal end of the outer tube 5. A tube is provided at the proximal end of the tube assembly, which is air-tightly connected to the tube assembly. The end of the tube is fixed to a cleaning valve 12. A hemostasis apparatus is provided at the proximal end within the tube assembly. In one embodiment, the hemostasis apparatus is a hemostasis ring 31.

At the distal end of the housing 9 is a fixed sleeve 8. The tube assembly passes through the fixed sleeve 8 and extends into the interior of the rotation driving assembly. The rotation driving assembly includes a housing 9, a manual knob 11 disposed outside of the housing 9, and an entire rotation handle assembly rotatably disposed within the housing 9.

The entire rotation handle assembly includes a driving gear 18 disposed at the proximal end within the housing 9, a driven wheel for outer screw 23, and a driven wheel for intermediate screw 17, which fit the driving gear 18. The driven wheel for the outer screw 23 is fixed to the proximal end of the outer screw 19. Outer threads are provided on the outer surface of the outer screw 19. In the initial state, the distal end of the outer screw 19 is threadably connected to the outer screw jaw 21, meanwhile the outer screw jaw 21 is fixed to the connection tube for outer tube 13, and meanwhile the connection tube for outer tube 13 is closely fixed to the outer tube 5. The driven wheel for the intermediate screw 17 is fixed to the proximal end of the intermediate screw 14. Outer threads are provided on the outer surface of the intermediate screw 14. In the initial state, the intermediate screw jaw 16 is threadably and adjacently connected to the proximal end of the intermediate screw, meanwhile the intermediate screw jaw 16 is fixed to the connection tube for intermediate tube 22. The connection tube for intermediate tube 22 is closely fixed to the intermediate tube 6 at the same time.

The outer wall of the connection tube for outer tube 13 has a groove 27 on a side adjacent to the intermediate screw jaw 16, for readily pushing the connection tube for intermediate tube 22. Left hand threads and right hand threads, both of which have directions opposite to each other, are respectively provided on the outer screw 19 and the intermediate screw 14. In one embodiment, the thread pitch of the left hand threads is different from that of the right hand threads.

A guide groove for outer screw jaw 24 is provided within the housing 9. A connection apparatus for outer screw jaw 20 is configured on the outer screw jaw 21, such that the outer screw jaw 21 moves along the guide groove for outer screw jaw 24. A guide groove for intermediate screw jaw 25 is also provided within the housing 9. A connection apparatus for intermediate screw jaw 15 is configured on the intermediate screw jaw 16, such that the intermediate screw jaw 16 moves along the guide groove for intermediate screw jaw 25.

Figure 7:
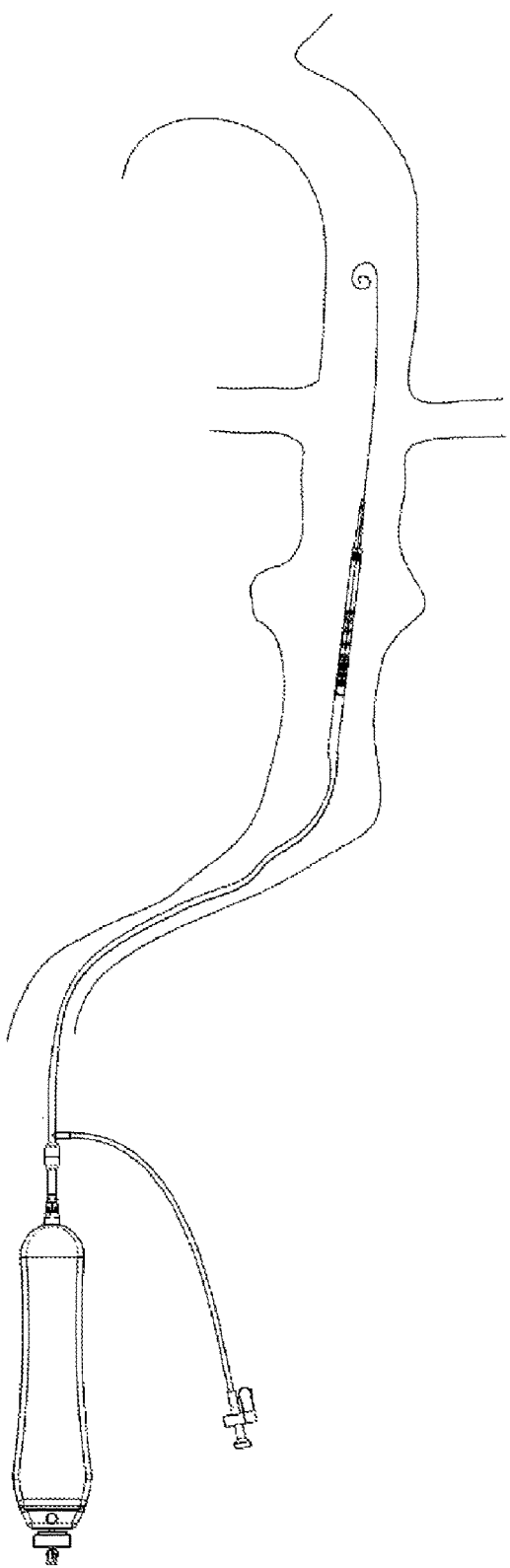
FIG. 7 is a schematic drawing of implantation of the delivery system into the vessels.
Figure 8:
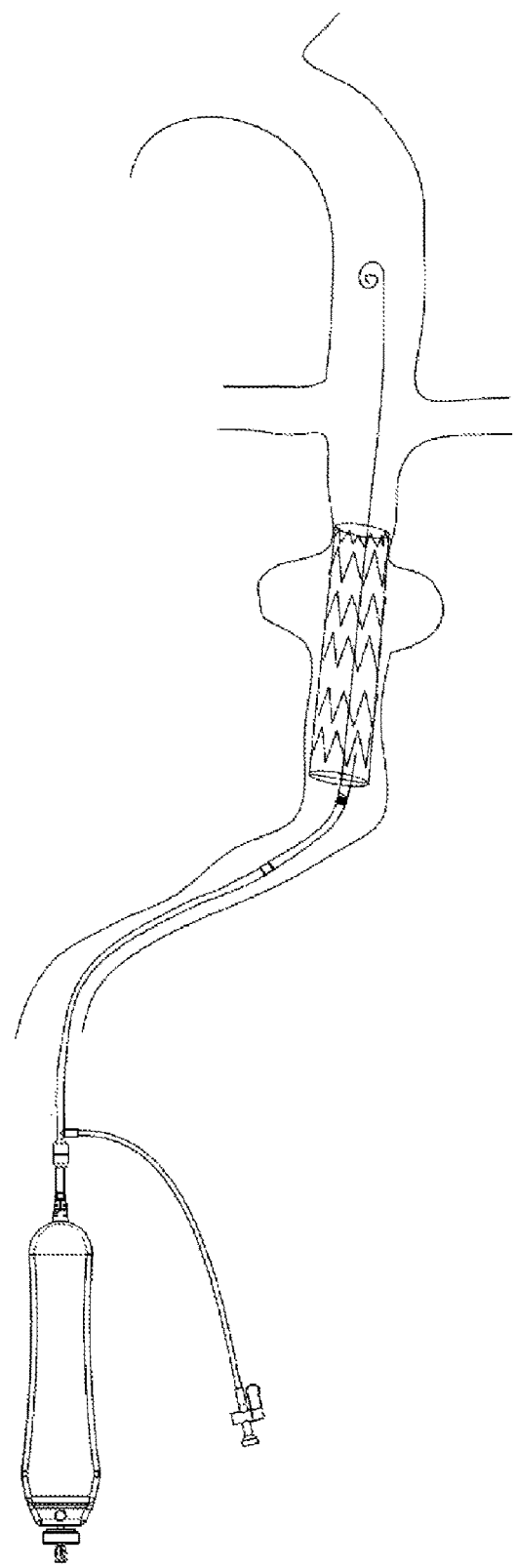
FIG. 8 is a schematic drawing of implantation of the intravascular stent into the vessels by using the delivery system.

Referring to FIGS. 7 and 8, the process of the present invention can be described in details as follows.

Firstly, the guide wire extends from tube sleeve 26 into the inner tube 7, and extends out of the distal end of the inner tube 7. Then the guide wire passes through vessels to direct the route for implanting the stent. The tube assembly is delivered to the target treatment site within the individual's vessel along the guide wire. The presence of the tube assembly at the target treatment site is indicated by the radiopaque ring 2. At this time, the locking screw 10 is released and the manual knob 11 is rotated to allow the driving gear 18 to rotate, so as to force the driven wheel for the outer screw 23 and the driven wheel for the intermediate screw 17 to rotate. Further, the driven wheel for the outer screw 23 drives the outer screw 19 to rotate. The driven wheel for the intermediate screw 17 drives the intermediate screw 14 to rotate in a direction opposite to the rotation direction of the outer screw 19. Further, the rotation of the outer screw 19 drives the outer screw jaw 21 to move to the proximal end along the guide groove for the outer screw jaw 24 under the limitation of the connection apparatus for outer screw jaw 20, that is to say, the outer tube 5 moves toward the proximal end. The rotation of the intermediate screw 14 drives the intermediate screw jaw 16 to move to the distal end along the guide groove for the intermediate screw jaw 25 under the limitation of the connection apparatus for intermediate screw jaw 15. In other words, the intermediate tube 6 moves toward the distal end, such that the intermediate tube 6 pushes the stent retaining block 4 and the intravascular stent 3 to move toward the distal end. When the thread pitch of the left hand threads provided on the outer screw 19 is different from that of the right hand threads provided on the intermediate screw 14, the movement speed of the intermediate tube 6 is different from that of the outer tube 5.

During movement, the connection tube for outer tube crosses with the connection tube for intermediate tube, forming a groove 27 on a side of the connection tube for outer tube, adjacent to the intermediate screw jaw 16, for readily pushing the connection tube for intermediate tube. During implantation, the hemostasis ring 31 can be used for stopping bleeding at any time. Meanwhile, medicaments can be injected into the body as needed through the guide tube and the cleaning valve 12 connected to the guide tube. The guide tube and the cleaning valve 12 connected to the guide tube can also be used to clean the delivery system for the intravascular stent. As such, the intravascular stent 3 can be pushed out of the outer tube 5 and placed in the target treatment area, as shown in FIG. 8. When the intravascular stent 3 is completely implanted into the body, the tube assembly can be withdrawn out of the body of the patient by the rotation driving assembly.

Since the intravascular stent 3 has axial high retractability, in the initial state, the intravascular stent 3 is extended to the longest state and placed within the outer tube 5. When an operation is being performed, under the circumstance that the distal end of the intravascular stent is initially pushed out of the outer tube 5, the part pushed out of the outer tube has tendency to retract. Since the intermediate tube 6 pushes the intravascular stent 3 outward by the stent retaining block 4, the retraction length can offset the pushed distance. It should be noted that there is no possibility for the intravascular stent 3 to be deformed, because the intravascular stent 3 that is stretched to the longest state is pressed within the outer tube 5. Therefore, the intravascular stent 3 can be pushed out of the outer tube 5 by the stent retaining block 4.

In comparison with the prior art, this embodiment has a handle with effectively reduced length since the outer screw 19 is configured to be parallel with the intermediate screw 14. Similarly, the outer screw 19 can be configured to cross with the intermediate screw 14. FIGS. 3 to 8 show this embodiment of the delivery system. Variations can be made to this embodiment. An outer screw 19 or an intermediate screw 14 and a driving member for driving the outer screw 19 or the intermediate screw 14 can be alternatively provided within the housing 9 of the rotation driving assembly. Similarly, the outer surface of the outer screw 19 can be provided with outer threads, which can be threadably connected to the outer screw jaw 21. The outer screw jaw 21 can be fixed to the outer tube 5 through the connection tube for outer tube 13. The outer screw 19 is driven to rotate by the driving member, so as to drive the outer screw jaw 21 and the outer tube 5 to move toward the proximal end. When the intermediate tube 6 is fixed, the intravascular stent 3 can be allowed to be exposed out of the outer tube 5. Alternatively, the outer surface of the intermediate screw 14 can be provided with the outer threads, which can be threadably connected to the intermediate screw jaw 16 by threads. The intermediate screw jaw 16 can be fixed to the intermediate tube 6 through the connection tube for intermediate tube 22. The intermediate screw 14 is driven to rotate by the driving member, so as to drive the intermediate screw jaw 16 and the intermediate tube 6 to move toward the distal end. When the outer tube 5 is fixed, the intravascular stent 3 can be allowed to be exposed out of the outer tube 5. Of course, these two solutions can be considered a simple version, and their effect will be different than that of the other embodiments.

Figure 9:
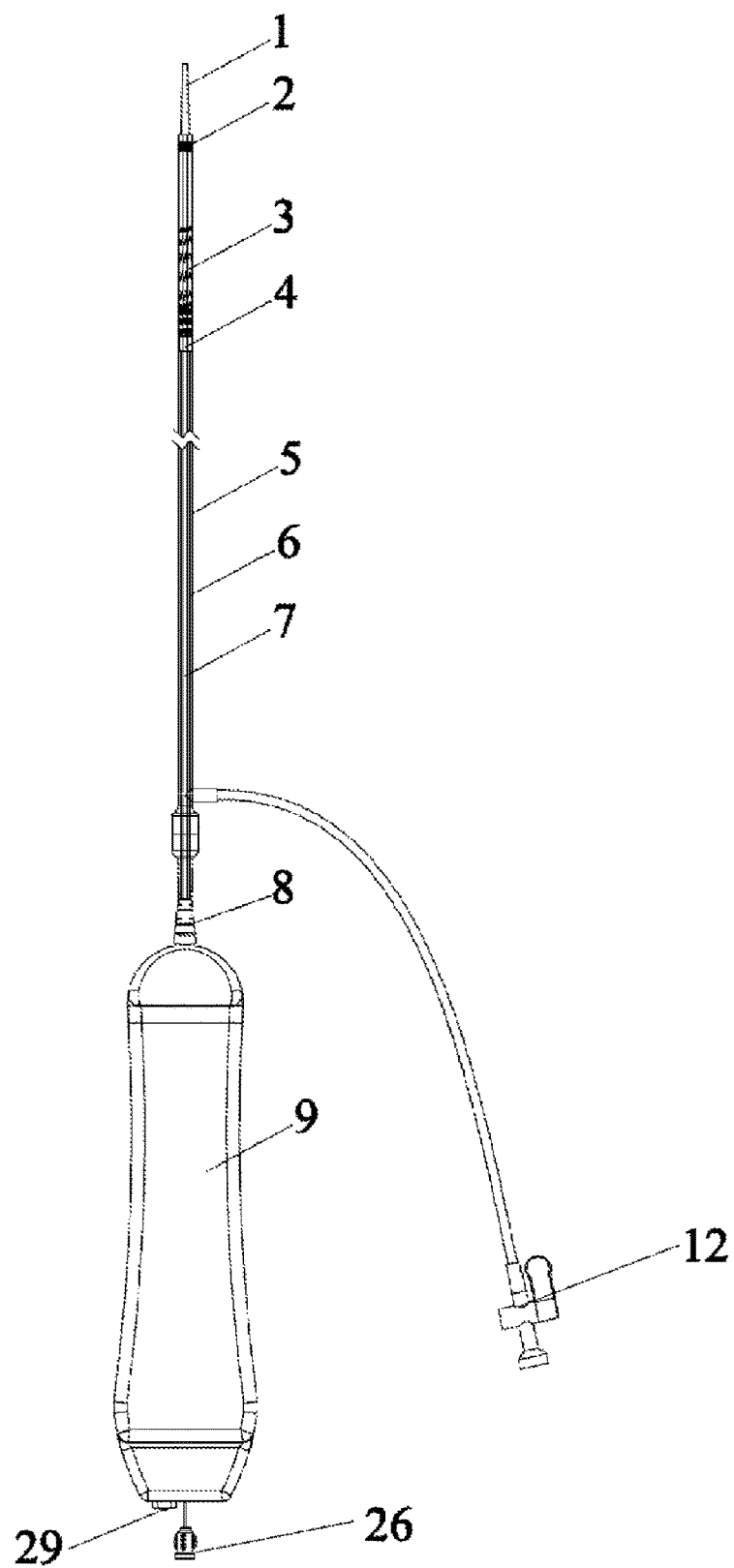
FIG. 9 is a schematic drawing according to a second embodiment.
Figure 10:
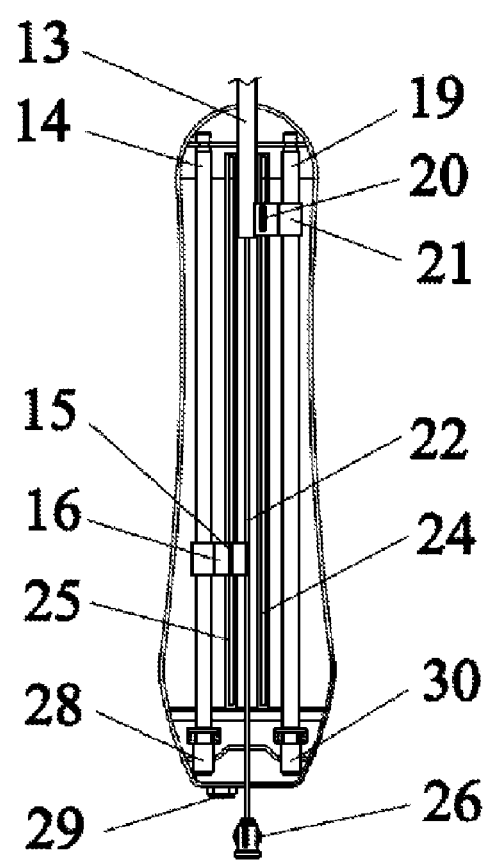
FIG. 10 is an inner structure schematic drawing of the rotation driving assembly.
Figure 11:
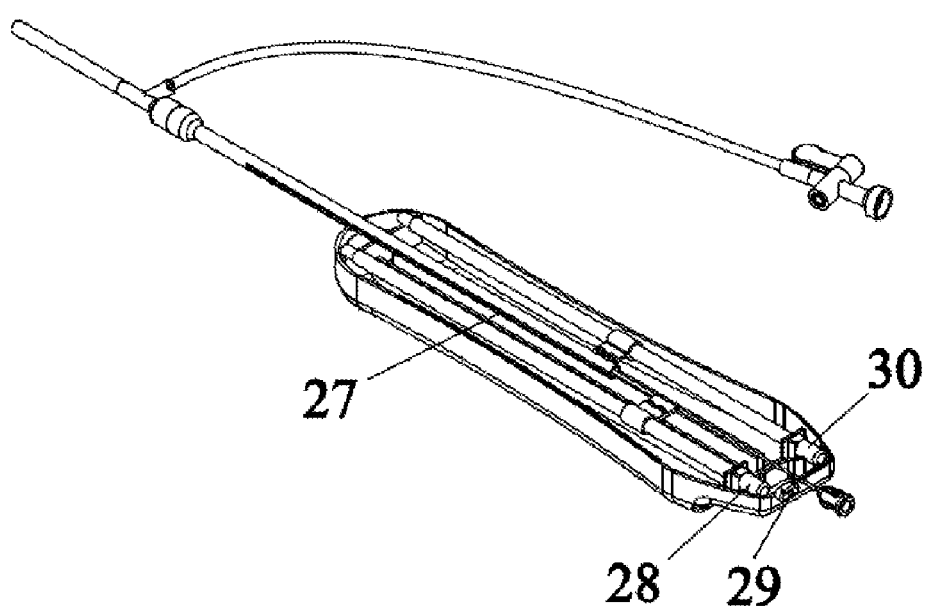
FIG. 11 is a three-dimensional structure drawing of the rotation driving assembly.

FIGS. 9 to 11 show the second embodiment. The second embodiment is different from the above embodiment in the driving member. In this embodiment, the driving member includes a second motor 30 and a first motor 28 respectively disposed on one end of the outer screw 19 and the intermediate screw 14. The second motor 30 and the first motor 28 are controlled by the switch 29 disposed outside of the housing 9. The process can be described as follows. Firstly, the guide wire extends from the tube sleeve 26 into the inner tube 7 and extends out of the distal end of the inner tube 7. Then the tube assembly of the delivery system can be introduced to the target treatment area by the introduction of the guide wire and tip 1. The arrival of the delivery system at target treatment area is indicated by radiopaque ring 2. At this time, the switch 29 is in ON state, the second motor 30 and the first motor 28 rotate. Further, the second motor 30 drives the outer screw 19 to rotate, and the first motor 28 drives the intermediate screw 14 to rotate at a direction opposite to the one at which the outer screw 19 rotates. The rotation of the outer screw 19 drives the outer screw jaw 21 to move toward the proximal end along the guide groove for the outer screw jaw 24 under the limitation of the connection apparatus for outer screw jaw 20, such that the outer tube 5 moves toward the proximal end. The rotation of the intermediate screw 14 drives the intermediate screw jaw 16 to move toward the distal end along the guide groove for the intermediate screw jaw 25 under the limitation of the connection apparatus for intermediate screw jaw 15, such that the intermediate tube 6 moves toward the distal end. Therefore, the intermediate tube 6 pushes the stent retaining block 4 and the intravascular stent 3 to move toward distal end. When the thread pitch of the left hand threads provided on the outer screw 19 is different from that of the right hand threads provided on the intermediate screw 14, the movement speed of the intermediate tube 6 is different from that of the outer tube 5.

The handle assembly of this example can be provided with a touch program disk. In comparison with the prior art, such a handle assembly has following advantages: (1) one handle assembly adapts to different stents with different retraction ratios by adjusting the rotation speed ratio of the motors, and/or (2) one intravascular stent which can be placed into vessels with different diameters has different retraction ratios. Therefore, the rotation speed ratio of the motors can be set according to the environment to perform increased accurate location.

The terms describing the location and the orientation refer to the operator of the device. The end close to the operator is the proximal end and the end far away from the operator is the distal end.

The present invention is not limited to the embodiments as mentioned above. For example, the cleaning valve 12 can be an adjustable air-tight one-way valve or otherwise. The hemostasis ring 31 can be other forms and can be placed in other positions in the system.

It should be understood that the present invention is described in the form of the aforesaid embodiments for the purpose of clarity, but each embodiment does not include only one independent solution. The skilled in the art should consider the present invention as a whole, solutions of each embodiment can be combined to create other embodiments that can be understood by the skilled in the art.

The detailed description as mentioned above merely illustrates the feasible embodiments of the present invention, but not intends to limit the scope of the present invention. The equivalent embodiments or variations that are made without departing from the spirit of the present invention come within the scope of the present invention.

The invention claimed is:

1. A highly retractable intravascular stent delivery system, including a tube assembly and a rotation driving assembly, wherein, the tube assembly extends into the rotation driving assembly and is driven by the rotation driving assembly, wherein the tube assembly includes an outer tube (5), an intermediate tube (6) disposed within the outer tube (5), and an inner tube (7) disposed within the intermediate tube (6), wherein the inner tube (7) includes a hollow channel through which guide wires pass; the delivery system is introduced to the target treatment area by the guide wires, and the outer tube (5) includes an intravascular stent loading area within which the intravascular stent (3) is placed; and a stent retaining block (4) is abutted against a proximal end of the intravascular stent (3), the stent retaining block (4) is fixed on a distal end of the intermediate tube (6); a distal end of the inner tube (7) passes through an inner cavity of the stent retaining block (4) and the intravascular stent (3) and extends out of a distal surface of the outer tube (5);

the rotation driving assembly includes a housing (9), an outer screw (19) and an intermediate screw (14) disposed within the housing (9) and a driving member for driving the outer screw (19) and the intermediate screw (14) to rotate, wherein outer threads are provided on an outer surface of the outer screw (19) that is threadably connected to an outer screw jaw (21), and the outer screw jaw (21) is non-movably connected to the outer tube (5) through a connection tube for the outer tube (5); outer threads are provided on an outer surface of the intermediate screw (14) that is threadably connected to an intermediate screw jaw (16), and the intermediate screw jaw (16) is non-movably connected to the intermediate tube (6) through a connection tube for the intermediate tube (22); the outer screw (19) and the intermediate screw (14) are respectively provided with left hand threads and right hand threads that are opposite to each other; the driving member drives the outer screw (19) and the intermediate screw (14) to rotate in opposite directions, and the rotation of the outer screw (19) drives the outer screw jaw (21) to move to the proximal end of the outer screw (19); and the rotation of the intermediate screw (14) drives the intermediate screw jaw (16) to move to the distal end of the intermediate screw (14), such that the intermediate tube (6) drives the stent retaining block (4) and the intravascular stent (3) to move to the distal end, wherein the outer screw (19) and the intermediate screw (14) are configured to be parallel with each other.

2. The highly retractable intravascular stent delivery system of claim 1, wherein the driving member includes a manual knob (11) for driving the rotation of a driving gear (18) positioned outside of the housing (9), and an entire rotation handle assembly rotatably disposed within the housing (9);

the entire rotation handle assembly includes the driving gear (18) located at the proximal end within the housing (9), an outer screw driven wheel (23) and an intermediate screw driven wheel (17), which are fitted with the driving gear (18);

the outer screw driven wheel (23) is non-movably connected to the proximal end of the outer screw (19), and the intermediate screw driven wheel (17) is non-movably connected to the proximal end of the intermediate screw (14).

3. The highly retractable intravascular stent delivery system of claim 1, wherein the driving member includes a second motor (30) disposed at the end of the outer screw (19), a first motor (28) disposed at the end of the intermediate screw (14) and a switch (29) disposed outside of the housing (9) for controlling the second motor (30) and the first motor (28).

4. The highly retractable intravascular stent delivery system of claim 3, wherein the thread pitch of the left hand threads provided on the outer screw (19) is different from that of the right hand threads provided on the intermediate screw (14).

5. The highly retractable intravascular stent delivery system of claim 1, wherein a locking screw (10) is configured outside of the housing (9) at the distal end.

6. The highly retractable intravascular stent delivery system of claim 1, wherein a guide groove for outer screw jaw (24) is configured within the housing (9), a connection apparatus for outer screw jaw (20) is configured on the outer screw jaw (21), such that the outer screw jaw (21) moves along the guide groove for outer screw jaw (24), a guide groove for intermediate screw jaw (25) is also configured within the housing (9), a connection apparatus for intermediate screw jaw (15) is configured on the intermediate screw jaw (16), such that the intermediate screw jaw (16) moves along the guide groove for intermediate screw jaw (25).

7. The highly retractable intravascular stent delivery system of claim 1, wherein
a groove (27) is formed on the outer wall of the connection tube for outer tube (13), adjacent to the intermediate screw jaw (16), for readily pushing the connection tube for intermediate tube (22).

8. The highly retractable intravascular stent delivery system of claim 1, wherein a tube sleeve (26) is non-movably disposed at the proximal end of the inner tube (7), such that guide wires extend into the inner tube (7) through the tube sleeve (26).

9. The highly retractable intravascular stent delivery system of claim 1, wherein a guide tube is disposed at a proximal end of the tube assembly, which is air-tightly connected to the tube assembly, and a cleaning valve (12) is air-tightly and non-movably connected to the guide tube.

10. The highly retractable intravascular stent delivery system of claim 1, wherein a hemostasis ring is disposed at a proximal end of the tube assembly.

11. A highly retractable intravascular stent delivery system, including a tube assembly and a rotation driving assembly, wherein, the tube assembly extends into the rotation driving assembly and is driven by the rotation driving assembly,
wherein the tube assembly includes an outer tube (5), an intermediate tube (6) and an inner tube (7), which are sleeved to each other, wherein the inner tube (7) includes a hollow channel through which guide wires pass; an intravascular stent (3) is disposed between the outer tube (5) and the inner tube (7), which is located at a distal end of the intermediate tube (6);
the rotation driving assembly includes a housing (9), an outer screw (19) and an intermediate screw (14) disposed within the housing (9), and a driving member for driving the outer screw (19) and the intermediate screw (14) to rotate, wherein, the outer screw (19) and the intermediate screw (14) are configured to be parallel with each other, the outer screw (19) includes left hand threads and the intermediate screw (14) includes right hand threads, the driving member drives the outer screw (19) and the intermediate screw (14) to rotate at directions opposite to each other, such that the outer screw (19) drives the outer tube (5) to move toward a proximal end of the outer screw (19), and the intermediate screw (14) drives the intermediate tube (6) to move toward a distal end of the intermediate screw (14), and further the intermediate tube (6) pushes the intravascular stent (3) to move toward the distal end of the intermediate tube (6).

12. The highly retractable intravascular stent delivery system of claim 11, wherein the outer tube (5) includes an intravascular stent loading area within which the intravascular stent (3) is placed; a stent retaining block (4) is abutted against the proximal end of the intravascular stent (3), the stent retaining block (4) is fixed on the distal end of the intermediate tube (6); the distal end of the inner tube (7) passes through the inner cavity of the stent retaining block (4) and the intravascular stent (3), and extends out of the distal surface of the outer tube (5).

13. The highly retractable intravascular stent delivery system of claim 11, wherein outer threads are provided on the outer surface of the outer screw (19) that is threadably connected to an outer screw jaw (21), the outer screw jaw (21) is non-movably connected to the outer tube (5) through a connection tube for the outer tube (13); outer threads are provided on the outer surface of the intermediate screw (14) that is threadably connected to an intermediate screw jaw (16), the intermediate screw jaw (16) is non-movably connected to the intermediate tube (6) through a connection tube for the intermediate tube (22); the rotation of the outer screw (19) drives the outer screw jaw (21) to move toward the proximal end of the outer screw (19) and the rotation of the intermediate screw (14) drives the intermediate screw jaw (16) to move toward the distal end of the intermediate screw (14).

14. The highly retractable intravascular stent delivery system of claim 11, wherein the driving member includes a manual knob (11) for driving the rotation of a driving gear (18), which is positioned outside of the housing (9), and an entire rotation handle assembly rotatably disposed within the housing (9), wherein the entire rotation handle assembly includes a driving gear (18) located at the proximal end within the housing (9), an outer screw driven wheel (23) and an intermediate screw driven wheel (17), which are fitted with the driving gear (18); the outer screw driven wheel (23) is non-movably connected to the proximal end of the outer screw (19), and the intermediate screw driven wheel (17) is non-movably connected to a proximal end of the intermediate screw (14).

15. The highly retractable intravascular stent delivery system of claim 11, wherein the driving member includes a second motor (30) disposed at an end of the outer screw (19), a first motor (28) disposed at an end of the intermediate screw (14) and a switch (29) disposed outside of the housing (9) for controlling the second motor (30) and the first motor (28).

16. A highly retractable intravascular stent delivery system, including a tube assembly and a rotation driving assembly, wherein, the tube assembly extends into the rotation driving assembly and is driven by the rotation driving assembly,
wherein the tube assembly includes an outer tube (5), an intermediate tube (6) disposed within the outer tube (5), and an inner tube (7) disposed within the intermediate tube (6), wherein the inner tube (7) includes a hollow channel through which guide wires pass, the delivery system is introduced to the target treatment area by the guide wires, and the outer tube (5) includes an intravascular stent loading area within which the intravascular stent (3) is placed; and a stent retaining block (4) is abutted against a proximal end of the intravascular stent (3), the stent retaining block (4) is fixed to the distal end of the intermediate tube (6); a distal end of the inner tube (7) passes through the inner cavity of the stent retaining block (4) and the intravascular stent (3) and extends out of a distal surface of the outer tube (5);

the rotation driving assembly includes a housing (9), an outer screw (19) or an intermediate screw (14) disposed within the housing (9) and a driving member for driving the outer screw (19) or the intermediate screw (14) to rotate, wherein outer threads are provided on the outer surface of the outer screw (19) that is threadably connected to an outer screw jaw (21), and the outer screw jaw (21) is non-movably connected to the outer tube (5) through a connection tube for the outer tube (13); outer threads are provided on the outer surface of the intermediate screw (14) that is threadably connected to an intermediate screw jaw (16), and the intermediate screw jaw (16) is non-movably connected to the intermediate tube (6) through a connection tube for the intermediate tube (22); the driving member drives respectively the outer screw (19) or the intermediate screw (14) to rotate in directions opposite to each other, and the rotation of the outer screw (19) drives the outer screw jaw (21) and the outer tube (5) to move to the proximal end; and the rotation of the intermediate screw (14) drives the intermediate screw jaw (16) and the intermediate tube (6) to move to a distal end, wherein the outer screw (19) and the intermediate screw (14) are configured to be parallel with each other.

17. The highly retractable intravascular stent delivery system of claim 16, wherein the driving member includes a manual knob (11) for driving the rotation of a driving gear (18), which is positioned outside of the housing (9), and an entire rotation handle assembly rotatably disposed within the housing (9), wherein the entire rotation handle assembly includes a driving gear (18) located at the proximal end within the housing (9), a driven wheel for the outer screw (23) and a driven wheel for the intermediate screw (17), which are fitted with the driving gear (18); the driven wheel for the outer screw (23) is non-movably connected to a proximal end of the outer screw (19), and the driven wheel for the intermediate screw (17) is non-movably connected to a proximal end of the intermediate screw (14).

18. The highly retractable intravascular stent delivery system of claim 16, wherein the driving member includes a second motor (30) disposed at an end of the outer screw (19), a first motor (28) disposed at an end of the intermediate screw (14) and a switch (29) disposed outside of the housing (9) for controlling the second motor (30) and the first motor (28).

* * * * *